United States Patent [19]

Furukawa et al.

[11] Patent Number: 5,017,483

[45] Date of Patent: May 21, 1991

[54] PROCESS FOR PRODUCING L-THREONINE

[75] Inventors: Satoru Furukawa; Akio Ozaki; Toshihide Nakanishi; Yukinobu Kotani, all of Hofu; Masahiro Sugimoto, Chiba, all of Japan

[73] Assignee: Kyowa Hakko Kogyo Co., Ltd., Tokyo, Japan

[21] Appl. No.: 13,797

[22] Filed: Feb. 12, 1987

[30] Foreign Application Priority Data

Feb. 20, 1986 [JP] Japan .................................. 61-36164
Feb. 20, 1986 [JP] Japan .................................. 61-36165
Jul. 10, 1986 [JP] Japan .................................. 61-162569
Dec. 19, 1986 [JP] Japan .................................. 61-303138

[51] Int. Cl.$^5$ ........................ C12P 13/08; C12N 1/20; C12N 15/00
[52] U.S. Cl. ................................ 435/115; 435/252.8; 435/172.1; 435/849
[58] Field of Search ..................... 435/115, 849, 252.8, 435/172.1

[56] References Cited

U.S. PATENT DOCUMENTS

| | | | |
|---|---|---|---|
| 3,494,830 | 2/1970 | Nakayama et al. ................. | 435/115 |
| 3,622,453 | 11/1971 | Akeyama ............................ | 435/849 |

FOREIGN PATENT DOCUMENTS

| | | | |
|---|---|---|---|
| 1484846 | 6/1967 | France . | |
| 1580549 | 9/1969 | France . | |
| 1010037 | 3/1981 | Japan ................................... | 435/115 |
| 0180597 | 9/1985 | Japan ................................... | 435/115 |
| 1342308 | 1/1974 | United Kingdom . | |
| 2072185 | 9/1981 | United Kingdom . | |

OTHER PUBLICATIONS

Chemical Abstracts, vol. 95, No. 5, Aug. 1981, p. 580, abstract No. 40855a, Columbus, Ohio, U.S., & JP-A-81 10 037, Kyowa Hakko Kogyo Co., Ltd., 05-03-1981.
Research and Development in Japan. Awarded the Okochi Memorial Prize, 1984, pp. 43-49, Okochi Memorial Found., Tokyo, JP; M. Kismi et al., "Development of New Ferment. Method for Amino Acid Production by Intracellular . . . ".
Stanbury et al., *Principles of Fermentation Technology*, Pergamon Press, 1984.
Cohen, G., In *Amino Acids: Biosynthesis and Genetic Regulation*, 1983, pp. 147-158.
Lynn et al., In *Amino Acids: Biosynthesis and Genetic Regulation*, 1983, pp. 173-185.
Sikyta, B., *Methods in Industrial Microbiology*, 1983, pp. 238-239.

*Primary Examiner*—Douglas W. Robinson
*Assistant Examiner*—Irene Marx
*Attorney, Agent, or Firm*—Antonelli, Terry, Stout & Kraus

[57] ABSTRACT

A process is disclosed for producing L-threonine. the process involves culturing in a medium a microorganism of the genus Escherichia capable of producing L-threonine which has resistance to at least one of rifampicin, lysine, methionine, aspartic acid and homoserine, or a decreased ability to degrade L-threonine, accumulating L-threonine in the culture liquor and recovering L-threonine therefrom.

7 Claims, 1 Drawing Sheet

United States Patent Office

PTO - BOYERS, PA Duty Station

MISSING PAGE TEMPORARY NOTICE

PATENT # 5017483   FOR ISSUE DATE 5-21-91

HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

DRAWING SHEET # 1

Data Conversion Operation
Boyers, Pa

PROCESS FOR PRODUCING L-THREONINE

BACKGROUND OF THE INVENTION

1. Field of the Invention

The present invention relates to a process for producing L-threonine, which is an amino acid useful as a medicament (e.g., an amino acid preparation), an additive for animal feed, etc.

2. Description of the Prior Art

Heretofore, various processes for producing L-threonine by fermentation have been known; for example, a process using a microorganism belonging to the genus Escherichia and having sensitivity to borrelidin (Japanese Published Examined Patent Application No. 6752/76), a process using a microorganism belonging to the genus Escherichia which requires diaminopimelic acid and methionine and of which threonine biosynthesis system is resistant to the feedback inhibition of threonine (Japanese Published Examined Patent Application No. 10037/81), a process using a microorganism belonging to the genus Serratia which is deficient in threonine-dehydrogenase and resistant to threonine metabolism-antagonist (Japanese Published Examined Patent Application No. 48195/77), a process using a microorganism belonging to the genus Corynebacterium and having resistance to α-amino-β-hydroxyvaleric acid and S-(2-aminoethyl)-L-cysteine, and a requirement for methionine (Japanese Published Unexamined Patent Application No. 19087/72), a process using a microorganism belonging to the genus Brevibacterium and having resistance to α-amino-β-hydroxyvaleric acid and S-(2-aminoethyl)-L-cysteine, and a requirement for leucine (Japanese Published Unexamined Patent Application No. 31093/75), a process using a microorganism belonging to the genus Brevibacterium and having resistance to α-amino-β-hydroxyvaleric acid and S-(2-aminoethyl)-L-cysteine, and requirements for L-isoleucine and L-lysine (Japanese Published Unexamined Patent Application No. 224684/83), etc.

However, the known processes are still insufficient in efficiency of the production of L-threonine.

It is therefore an object of the present invention to provide a process for producing L-threonine in higher yield and at low cost.

SUMMARY OF THE INVENTION

According to the present invention, L-threonine can be produced in high yield by using a microorganism of the genus Escherichia capable of producing L-threonine which has resistance to at least one of rifampicin, lysine, methionine, aspartic acid and homoserine, or a decreased ability to degrade L-threonine.

BRIEF DESCRIPTION OF THE DRAWING

FIG. 1 is a graph showing relative molar concentrations of threonine, glycine and isoleucine during the course of degradation reactions thereof utilizing Escherichia coli ATCC 21530. In the figure, —●— indicates the relative molar concentration of threonine (Thr), —▲— that of glycine (Gly) produced by the degradation of threonine, - - - △ - - - that of glycine (Gly), and —●— □ —● that of isoleucine (Ile).

DETAILED DESCRIPTION OF THE INVENTION

In the present invention, any microorganism belonging to the genus Escherichia can be used, provided that it is capable of producing L-threonine and has resistance to at least one of rifampicin, lysine, methionine, aspartic acid and homoserine, or a decreased ability to degrade L-threonine.

Suitable strains resistant to rifampicin can be obtained, for example by mutating an L-threonine-producing microorganism belonging to the genus Escherichia in accordance with a conventional mutation technique, culturing the resulting mutants in a minimal medium containing not less than 20 γ/ml rifampicin, and then recovering the mutants capable of growth on the rifampicin-containing medium. As an example of the suitable strain, rifampicin-resistant Escherichia coli H-4258 (FERM BP-985) (hereinafter referred to as H-4258) may be mentioned.

Suitable strains resistant to lysine, methionine, aspartic acid or homoserine can be obtained, for example, by mutating an L-threonine-producing microorganism of the genus Escherichia in accordance with a conventional mutation technique, culturing the resulting mutants in a minimal medium containing not less than 10 g/l lysine, methionine, aspartic acid or homoserine, and then recovering the mutants capable of growth on said medium.

Examples of the suitable strains include lysine-resistant Escherichia coli H-4435 (FERM BP-1094) (hereinafter referred to as H-4435), methionine-resistant Escherichia coli H-4436 (FERM BP-1095) (hereinafter referred to as H-4436), aspartic acid-resistant Escherichia coli H-4225 (FERM BP-1236) (hereinafter referred to as H-4225) and homoserine-resistant Escherichia coli H-4226 (FERM BP-1237) (hereinafter referred to as H-4226).

The expression "a microorganism having a decreased ability to degrade L-threonine" used herein means a microorganism having a reduced capability of degrading L-threonine into glycine. A microorganism belonging to the genus Escherichia degrades L-threonine via glycine, as is shown in Reference Example 1 given hereinbelow. Microoganisms having a decreased ability to degrade L-threonine can be obtained by mutating an L-threonine-producing microorganism in accordance with a conventional mutation technique, and then selecting a mutant having a decreased ability to degrade L-threonine into glycine, without deterioration in its ability to produce L-threonine. The ability to degrade L-threonine into glycine can be examined by carrying out the degradation of L-threonine in the manner shown in Reference Example 1 described hereinbelow, and then determining the residual amount of L-threonine by means of paper chromatography, high-pressure liquid chromatography, or the like. Increase of the residual amount of L-threonine means decrease of the ability of degrading L-threonine into glycine.

As the microorganism having a decreased ability to degrade L-threonine to be employed in the present invention, a microorganism of which ability to degrade L-threonine has been lowered to 50% or less of the parent strain, that is, a microorganism giving a residual L-threonine in an amount at least twice that of the parent strain is suitable. As an example of the suitable microorganism, Escherichia coli H-4257 (FERM BP-984) (hereinafter referred to as H-4257) may be mentioned.

Methods used to obtain the above-described suitable strains are explained below.

(1) Strain H-4258

*Escherichia coli* ATCC 21530 which requires diaminopimelic acid and methionine and is resistant to α-amino-β-hydroxylvaleric acid was subjected to a conventional mutation treatment utilizing N-methyl-N'-nitro-N-nitrosoguanidine (hereinafter referred to as NTG) (200 γ/ml, 30° C., 30 minutes). Then, the strain was smeared on a yeast bouillon agar medium (5 g/l meat extract, 10 g/l peptone, 5 g/l yeast extract, 2.5 g/l NaCl, 0.1 g/l diaminopimelic acid and 20 g/l agar, pH 7.2) containing 100 γ/ml rifampicin, and cultured at 30° C. for 2 to 6 days to obtain colonies of rifampicin-resistant mutants growable thereon. Fifty strains of rifampicin-resistant mutants were picked up and subjected to the L-threonine production test as shown in Example 1 to select the strains having an L-threonine-producing ability greater than that of the parent strain. The strain H-4258 is one of the thus obtained mutants. It was deposited on Feb. 13, 1986 with the Fermentation Research Institute, Agency of Industrial Science and Technology, Japan (hereinafter referred to as FRI), under deposition number of FERM BP-985.

(2) Strains H-4435 and H-4436

*Escherichia coli* ATCC 21530 was subjected to a conventional mutation treatment utilizing NTG (200 γ/ml, 30° C., 30 minutes). Then, the strain was smeared on a minimal medium [0.5% glucose, 0.1% $(NH_4)_2SO_4$, 0.7% $K_2HPO_4$, 0.2% $KH_2PO_4$, 0.1 g/l $MgSO_4.7H_2O$, 20 mg/l $Fe_2(SO_4)_3$, 50 mg/l diaminopimelic acid, 50 mg/l methionine and 2% agar, pH 7.2] containing 15 g/l lysine or methionine, and cultured at 30° C. for 2 to 6 days to obtain colonies of lysine- or methionine-resistant mutants growable thereon. Fifty strains each of lysine-resistant mutants and methionine-resistant mutants were picked up and subjected to the L-threonine production test as shown in Example 1 to select the strains having an L-threonine-producing ability greater than that of the parent strain. Among the thus selected strains are H-4435 which is resistant to lysine and H-4436 which is resistant to methionine. These strains were deposited with the FRI on June 28, 1986 under deposition numbers FERM BP-1094 and FERM BP-1095, respectively.

(3) Strains H-4225 and H-4226

The aspartic acid-resistant strain, H-4225, and the homoserine-resistant strain, H-4226, were obtained in the same manner as in paragraph (2) above, except that 15 g/l aspartic acid or homoserine was used in place of 15 g/l lysine or methionine. These strains were deposited with the FRI on Dec. 17, 1986 under deposition numbers FERM BP-1236 and FERM BP-1237, respectively.

(4) Strain H-4257

*Escherichia coli* ATCC 21530 was subjected to a conventional mutation treatment utilizing NTG (200 γ/ml, 30° C., 30 minutes), and cultured on a minimal medium (0.5% glucose, 0.1% $(NH_4)_2SO_4$, 0.7% $K_2HPO_4$, 0.2% $KH_2PO_4$, 0.1 g/l $MgSO_4.7H_2O$, 20 mg/l $Fe_2(SO_4)_3$, 50 mg/l diaminopimelic acid and 50 mg/l methionine). Strains which grew well on the medium were picked up and then cultured on a medium containing L-threonine as the sole nitrogen source and having the same composition as that of the above minimal medium, except that 0.2% L-threonine was incorporated thereinto instead of 0.1% $(NH_4)_2SO_4$. Two hundred strains very poorly growable on the medium were selected.

These strains were subjected to the L-threonine degradation test in a similar manner as in Reference Example 1. Almost all the strains had a lower ability to degrade L-threonine into glycine than the parent strain. Thirty strains having a markedly decreased ability to degrade L-threonine were selected. They were subjected to the L-threonine production test shown in Example 1, and the strains having a markedly improved ability to produce L-threonine were selected. The strain H-4257 is one of the thus selected strains.

This strain was deposited with the FRI on Feb. 13, 1986 under deposition number of FERM BP-984.

In the present invention, either a synthetic medium or a natural medium can be used so long as it contains carbon sources, nitrogen sources, inorganic salts, growth factors, and the like.

As the carbon sources, hydrocarbons such as glucose, fructose, molasses and starch hydrolyzate; and organic acids such as acetic acid, propionic acid, formic acid, fumaric acid and malic acid, etc. may be used.

As the nitrogen sources, ammonia, ammonium chloride, ammonium sulfate, ammonium acetate, ammonium phosphate, peptone, meat extract, yeast extract, corn steep liquor, casein hydrolyzate, acid hydrolyzate of soy bean cake, various microbial cells, digest of microbial cells, etc., may be used.

As the inorganic salts, potassium dihydrogenphosphate, potassium hydrogenphosphate, magnesium phosphate, magnesium sulfate, sodium chloride, ferrous sulfate, manganese sulfate, copper sulfate, calcium carbonate, etc. may be used.

As the growth factors, amino acids (e.g., D,L-methionine), diaminopimelic acid, etc. may be used.

Culturing is carried out under aerobic conditions, e.g., by shaking culture, agitation submerged culture, etc. at a temperature of 20° to 40° C., preferably 25° to 35° C. The pH of the medium is in the range of 5 to 9, and is preferably maintained at around neutrality. The pH is adjusted with calcium carbonate, organic or inorganic acids, alkali solutions, ammonia, pH buffering agent, etc.

A substantial amount of L-threonine is usually produced and accumulated in the resulting culture liquor after 2 to 7 days of culturing.

After the completion of culturing, precipitates such as cells are removed from the culture liquor by means of centrifugation, etc. and L-threonine is recovered therefrom by means of ion exchange treatment, concentration, adsorption, salting-out or combinations thereof.

The present invention is illustrated by the following Examples and Reference Example.

Example 1

L-threonine production test was carried out using H-4258 strain as the seed strain.

The seed strain was cultured with shaking at 30° C. for 16 hours in a seed medium (pH 7.4) having a composition of 2% glucose, 1% peptone, 1% yeast extract, 0.25% NaCl and 0.1 g/l diaminopimelic acid. The resultant seed culture (2 ml) was inoculated into a 250 ml-Erlenmeyer flask containing 20 ml of fermentation medium (pH 7.4) comprising 7% glucose, 1.4% $(NH_4)_2SO_4$, 0.2% $KH_2PO_4$, 0.1% $MgSO_4.7H_2O$, 300 γ/ml diaminopimelic acid, 100 γ/ml D,L-methionine, 0.2% corn steep liquor and 3% $CaCO_3$, and cultured with shaking at 30° C. for 72 hours. L-threonine was produced in an amount of 18.6 g/l. As a control, the above procedure was repeated using the parent strain, ATCC 21530, whereby L-threonine was produced in an amount of 15.8 g/l.

The L-threonine-containing fermentation broth (200 ml) obtained by the use of H-4258 strain was then subjected to centrifugation (3,000 rpm, 10 minutes) to remove microbial cells and other impurities. The supernatant obtained was passed through a column of $H^+$-type Diaion SKI (highly acidic cation exchange resin manufactured by Mitsubishi Chemical Industries Ltd.) to adsorb L-threonine. The column was washed with water and eluted with 0.5N aqueous ammonia. Fractions containing L-threonine were combined and concentrated under reduced pressure. Then, ethanol was added and the mixture was stored under cooling to give 2.1 g of L-threonine.

Example 2

The same culturing procedure as in Example 1 was repeated, except that H-4435, H-4436 and ATCC 21530 strains were used as the seed strains in place of H-4258 strain. The results are shown in Table 1.

TABLE 1

| Strain | L-threonine Produced (g/l) |
|---|---|
| H-4435 | 18.7 |
| H-4436 | 18.9 |
| ATCC 21530 | 15.8 |

The fermentation broth of the strain H-4435 was treated in the same manner as in Example 1 and, as a result, 2.1 g of L-threonine was obtained.

Example 3

The same culturing procedure as in Example 1 was repeated except that H-4425, H-4426 and ATCC 21530 strains were used as the seed strains in place of H-4258 strain. The results are shown in Table 2.

TABLE 2

| Strain | L-threonine Produced (g/l) |
|---|---|
| H-4225 | 19.1 |
| H-4226 | 19.2 |
| ATCC 21530 | 15.9 |

The fermentation broth of the strain H-4426 was treated in the same manner as in Example 1 and, as a result, 2.1 g of L-threonine was obtained.

Example 4

The same culturing procedure as in Example 1 was repeated except that H-4257 and ATCC 21530 strains were used as the seed strains in place of H-4258 strain. In the fermentation broths obtained were contained 17.3 g/l and 15.8 g/l L-threonine, respectively.

The fermentation broth of the strain H-4257 was treated in the same manner as in Example 1 and, as a result, 1.9 g of L-threonine was obtained.

Example 5

In this example, H-4257 strain was used as the seed strain. The strain was cultured with shaking at 30° C. for 16 hours in a seed medium (pH 7.4) comprising 2% glucose, 1% peptone, 1% yeast extract, 0.25% NaCl and 0.1 g/l diaminopimelic acid. Two hundred ml of the thus obtained seed culture was subjected to centrifugation to collect microbial cells. After being washed, the cells were suspended in 20 ml of 0.1M phosphate buffer (pH 6.7) containing 10 g/l L-threonine and 1 g/l magnesium sulfate, and then subjected to rotary shaking (220 rpm) at 30° C. for 8 hours in a 300 ml-Erlenmeyer flask to give a residual amount of L-threonine of 7.2 g/l. As a control, the above procedure was repeated using the parent strain, ATCC 21530, whereby a residual amount of L-threonine of 0.5 g/l was obtained.

Reference Example 1

The pathway of the degradation of L-threonine with ATCC 21530 strain was examined in the following manner. The strain was washed with physiological saline, suspended in 20 ml of phosphate buffer (pH 6.7) containing 1% L-threonine, and then subjected to rotary shaking (220 rpm) in a 300 ml-Erlenmeyer flask. As shown in FIG. 1, L-threonine was almost completely degraded in 8 hours, and glycine was accumulated in substantial quantities (indicated by the solid line). The same procedure as above was repeated except that 1% glycine or L-isoleucine was used in place of L-threonine, whereby about 34% of glycine was degraded (indicated by the dotted line in FIG. 1) and L-isoleucine was not degraded at all (indicated by the dot-dash-line in FIG. 1).

It would be apparent from the above results that the degradation of L-threonine with the strain ATCC 21530 mainly proceeds via glycine. It is therefore possible to obtain L-threonine in high yield by using an L-threonine-producing microorganism having a decreased ability to degrade L-threonine into glycine.

What is claimed is:

1. A process for producing L-threonine which comprises culturing in a medium *Escherichia coli* H-4258 (FERM BP-985), H-4435 (FERM BP-1094), H-4436 (FERM BP-1095), H-4225 (FERM BP-1236), H-4226 (FERM BP-1237) or H-4257 (FERM BP-984), accumulating L-threonine in the culture liquor and recovering L-threonine therefrom.

2. A process for producing L-threonine which comprises culturing in a medium *Escherichia coli* H-4258 (FERM BP-985), accumulating L-threonine in the culture liquor and recovering L-threonine therefrom.

3. A process for producing L-threonine which comprises culturing in a medium *Escherichia coli* H-4435 (FERM BP-1094) or H-4436 (FERM BP-1095), accumulating L-threonine in the culture liquor and recovering L-threonine therefrom.

4. A process for producing L-threonine which comprises culturing in a medium *Escherichia coli* H-4225 (FERM BP-1236) or H-4226 (FERM BP-1237), accumulating L-threonine in the culture liquor and recovering L-threonine therefrom.

5. A process for producing L-threonine which comprises culturing in a medium *Escherichia coli* H-4257 (FERM BP-984), accumulating L-threonine in the culture liquor and recovering L-threonine therefrom.

6. A process according to claim 1 wherein said culturing is conducted at 20° to 40° C. for 2 to 7 days.

7. A biologically pure culture of the microorganism *Escherichia coli* which is a member selected from the group consisting of FERM BP-985, FERM BP-1094, FERM BP-1095, FERM BP-1236, FERM BP-1237 and FERM BP-984, which culture possesses an ability to produce L-threonine.

* * * * *